United States Patent
Armour et al.

[11] Patent Number: 6,020,346
[45] Date of Patent: *Feb. 1, 2000

[54] PIPERIDINE DERIVATIVES HAVING TACHYKININ ANTAGONIST ACTIVITY

[75] Inventors: Duncan Robert Armour; Gerard Martin Paul Giblin; Andrew Michael Kenneth Pennell; Peter John Sharratt, all of Stevenage, United Kingdom

[73] Assignee: Glaxo Wellcome Inc., Research Triangle Park, N.C.

[*] Notice: This patent is subject to a terminal disclaimer.

[21] Appl. No.: 08/849,727

[22] PCT Filed: Jan. 10, 1996

[86] PCT No.: PCT/EP96/00082

§ 371 Date: Jul. 8, 1997

§ 102(e) Date: Jul. 8, 1997

[87] PCT Pub. No.: WO96/21661

PCT Pub. Date: Jul. 18, 1996

[30] Foreign Application Priority Data

Jan. 12, 1995 [GB] United Kingdom .................. 9500549
Mar. 21, 1995 [GB] United Kingdom .................. 9505639
Mar. 21, 1995 [GB] United Kingdom .................. 9505640

[51] Int. Cl.[7] .................... A61K 31/445; C07D 40/10
[52] U.S. Cl. .................... 514/326; 514/329; 546/210; 546/223
[58] Field of Search ................. 514/326, 329; 546/210, 223

[56] References Cited

U.S. PATENT DOCUMENTS 5,703,240 12/1997 Armour et al. ................. 546/210
5,773,450 6/1998 Lowe et al. ................. 514/329

FOREIGN PATENT DOCUMENTS

93/00331 1/1993 WIPO .
93/01170 1/1993 WIPO .
95/08549 3/1995 WIPO .

OTHER PUBLICATIONS

Maggie "Tachykinin receptors and tachykinin receptor antagonists" J. Auton. Pharm. v. 13, p. 23–39, 1993.
Ward et al., *J. Med. Chem.,* vol. 38, No. 26, pp. 4985–4992, (1995).

*Primary Examiner*—Ceila Chang
*Attorney, Agent, or Firm*—Bacon & Thomas PLLC

[57] ABSTRACT

The present invention relates to piperidine derivatives of formula (I):

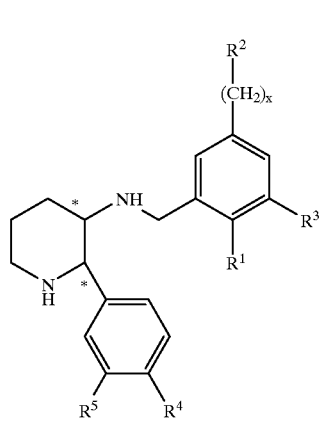

wherein the substituents $R^1$, $R^3$, $R^4$ and $R^5$ are as defined in the specification and claims, and the substituent $R^2$ is

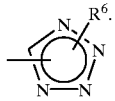

The pharmaceutically acceptable salts and solvates of these piperidine derivatives are also described. The invention also relates to processes for the preparation of the piperidine derivatives, and to their use in the treatment of conditions mediated by tachykinins.

8 Claims, No Drawings

PIPERIDINE DERIVATIVES HAVING TACHYKININ ANTAGONIST ACTIVITY

The present invention relates to piperidine derivatives, to processes for their preparation, pharmaceutical compositions containing them and their medical use.

3-Aminopiperidine derivatives described as having substance P antagonist activity are disclosed in, for example, PCT Patent Applications WO93/00331, WO93/01170 and WO94/13663.

In particular the invention relates to novel compounds which are potent and specific antagonists of tachykinins, including substance P and other neurokinins.

The present invention provides compounds of formula (I)

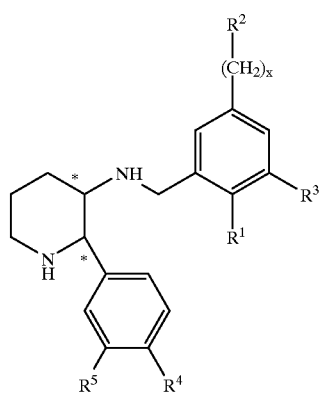

(I)

wherein $R^1$ is $-O-(CH_2)_p C_{3-7}$cycloalkyl, $-O-C_{1-7}$fluoroalkyl, or $-O-(CH_2)_n X$;

$R^2$ is

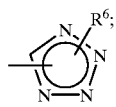

$R^3$ is a hydrogen or halogen atom;

$R^4$ and $R^5$ may each independently represent a hydrogen or halogen atom, or a $C_{1-4}$alkyl, $C_{1-4}$alkoxy or trifluoromethyl group;

X is selected from $C(O)-NR^7R^8$, $C(O)R^9$, $NR^7R^8$, $SO_2NR^7R^8$, $NHSO_2R^9$, $S(O)_s R^9$, $OC_{1-4}$alkyl, $NO_2$, $CO_2H$, $CO_2C_{1-4}$alkyl, CN or, when n is 2, X may also represent OH, SH or $NH_2$;

$R^6$ is a hydrogen atom, a $C_{1-4}$alkyl, $(CH_2)_m$cyclopropyl, $-S(O)_s C_{1-4}$alkyl, phenyl, $NR^{10}R^{11}$, $CH_2C(O)CF_3$, trifluoromethyl, difluoromethyl or cyano group;

$R^7$ and $R^8$ may each independently represent hydrogen atoms or a $C_{1-4}$alkyl group;

$R^9$ represents a $C_{1-4}$alkyl or trifluoromethyl group;

$R^{10}$ and $R^{11}$ may each independently represent a hydrogen atom, or a $C_{1-4}$alkyl or acyl group;

x represents zero or 1;

n is 1 or 2;

s represents zero, 1 or 2;

m represents zero or 1;

p represents zero or 1;

and pharmaceutically acceptable salts and solvates thereof.

Suitable pharmaceutically acceptable salts of the compounds of general formula (I) include acid addition salts formed with pharmaceutically acceptable organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. Dihydrochloride salts are particularly suitable.

Other acids, such as oxalic, while not in themselves pharmaceutically acceptable, may be useful in the preparation of salts useful as intermediates in obtaining the compounds of formula (I) and their pharmaceutically acceptable acid addition salts.

The solvates may, for example, be hydrates.

References hereinafter to a compound according to the invention includes both compounds of formula (I) and their pharmaceutically acceptable acid addition salts together with pharmaceutically acceptable solvates.

It will be appreciated by those skilled in the art that the compounds of formula (I) contain at least two chiral centres (shown as * in formula (I)) and thus exist in the form of two pairs of optical isomers (i.e. enantiomers) and mixtures thereof including racemic mixtures.

For example the compounds of formula (I) may be either cis isomers, as represented by figures (a) and (b), or trans isomers, as represented by figures (c) and (d), or mixtures thereof.

All of the isomers of the compounds of formula (I) represented by the figures (a) to (d) and mixtures thereof including racemic mixtures are included within the scope of the invention.

(a)
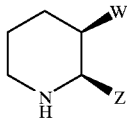

(b)
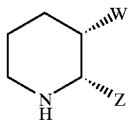

(c)
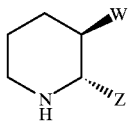

(d)
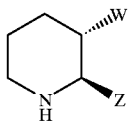

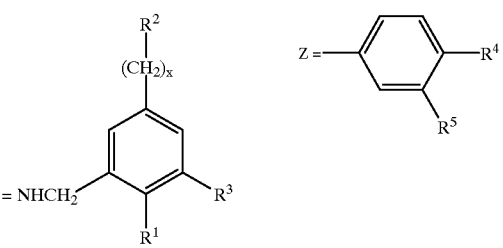

The compounds of formula (I) are preferably in the form of their cis isomers (i.e. as represented by figures (a) and (b)). The 2S, 3S isomers (i.e. as represented by figure (b)) are particularly preferred.

Referring to the general formula (I), a $C_{1-4}$alkoxy group may be a straight chain or branched chain alkoxy group, for example, methoxy, ethoxy, propoxy, prop-2-oxy, butoxy, but-2-oxy, 2-methylprop-1-oxy or 2-methylprop-2-oxy. A $C_{1-4}$alkyl group may be a straight chain or branched chain alkyl group and may be, for example, methyl, ethyl, propyl, prop-2-yl, butyl, but-2-yl, 2-methylprop-1-yl or 2-methylprop-2-yl. An —O—$(CH_2)_p C_{3-7}$-cycloalkyl group may be, for example cyclopropyloxy, cyclopropylmethyloxy, cyclobutyloxy, cyclobutylmethyloxy, cyclopentyloxy, cyclohexyloxy or cycloheptyloxy.

Referring to the general formula (I), an —O—$C_{1-7}$fluoroalkyl group may contain 1, 2 or 3 fluorine atoms and the $C_{1-7}$alkyl chain may be straight or branched. Examples of suitable groups include fluoromethyloxy, difluoromethyloxy, trifluoromethyloxy and 2,2,2-trifluoroethyloxy.

Referring to the general formula (I), when $R^7$, $R^8$, or $R^9$ represents a $C_{1-4}$alkyl group, this is suitably methyl.

Referring to the general formula (I), a halogen atom may be a fluorine, chlorine, bromine or iodine atom, such as a fluorine, chlorine or bromine atom.

Referring to the general formula (I), $R^1$ is suitably —O—$(CH_2)_n X$ where X is suitably a group selected from C(O)NHMe, C(O)NH$_2$, C(O)NMe$_2$, C(O)Me, C(O)CF$_3$, NHMe, NMe$_2$, SO$_2$NH$_2$, SO$_2$NHMe, SO$_2$NMe$_2$, NHSO$_2$Me, NHSO$_2$CF$_3$, S(O)$_s$Me or S(O)$_s$CF$_3$, for example where s is 2, OMe, NO$_2$, CO$_2$H, CO$_2$Me, CN or, when n is 2, X is suitably OH, SH or NH$_2$.

X is preferably OC$_{1-4}$ alkyl, for example OMe.

Referring to the general formula (I), $R^1$ is suitably a —O—$(CH_2)_p$-cyclopropyl, —O—$(CH_2)_p$-cyclopentyl, —O—$C_{1-4}$fluoroalkyl or O—$(CH_2)_n OC_{1-4}$alkyl group, such as cyclopropylmethyloxy, cyclopentyloxy, fluoromethyloxy, difluoromethyloxy, trifluoromethyloxy, 2,2,2-trifluoroethyloxy, especially fluoromethyloxy, O—$(CH_2)_n$ OMe, for example OCH$_2$OMe or O—CH$_2$CH$_2$OMe.

Referring to the general formula (I), $R^2$ is suitably a group

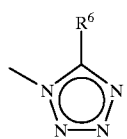

(A)

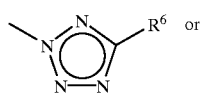

(B) or

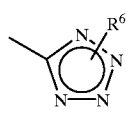

(C)

Referring to the general formula (I), when $R^6$ is an NR$^{10}$R$^{11}$ group; this is suitably NH$_2$, NH(C$_{1-4}$alkyl), NHacyl i.e. NHC(O)methyl, or N(C$_{1-4}$alkyl)$_2$.

Referring to the general formula (I), when $R^6$ is a $C_{1-4}$alkyl group, this is suitably methyl.

Referring to the general formula (I), when $R^2$ is a group (A) as defined above, $R^6$ is suitably a hydrogen atom or a $C_{1-4}$alkyl, e.g. methyl, or a trifluoromethyl group.

$R^2$ is preferably a group (A) as defined above.

$R^3$ is preferably a hydrogen atom.
$R^4$ and $R^5$ are preferably hydrogen atoms.
$R^6$ is preferably a hydrogen atom, a $C_{1-4}$alkyl, e.g. methyl, or a trifluoromethyl group.
x is preferably zero.

A preferred class of compounds of formula (I) are those wherein $R^1$ is —O—$(CH_2)_p C_{3-7}$cycloalkyl or —O—$C_{1-7}$fluoroalkyl, as defined hereinbefore, $R^2$ is

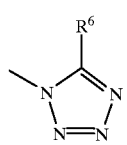

(A)

where $R^6$ is a hydrogen atom, a $C_{1-4}$alkyl, e.g. methyl, or trifluoromethyl group, x is zero and $R^3$, $R^4$ and $R^5$ are each hydrogen atoms.

A further preferred class of compounds of formula (I) are those wherein $R^1$ is a cyclopropylmethoxy, cyclopentyloxy, difluoromethyloxy, trifluoromethyloxy, 2,2,2-trifluoroethyloxy or, more preferably, a fluoromethyloxy group, $R^2$ is a group (A) as defined above, x is zero, $R^3$, $R^4$ and $R^5$ are hydrogen atoms, and $R^6$ is a hydrogen atom or a methyl or trifluoromethyl group.

A preferred class of compounds of formula (I) are those wherein $R^1$ is a group —O—$(CH_2)_n X$, $R^2$ is a group (A) as defined above, x is zero and $R^6$ is a hydrogen atom or a trifluoromethyl, difluoromethyl or cyano group.

An additional preferred class of compounds of formula (I) are those wherein $R^1$ is —O—$(CH_2)_n X$ where X is a group selected from C(O)NH$_2$, C(O)NHMe, C(O)NMe$_2$, C(O)Me, C(O)CF$_3$, NHMe, NMe$_2$, SO$_2$NH$_2$, SO$_2$NHMe, SO$_2$NMe$_2$, NHSO$_2$Me, NHSO$_2$CF$_3$, S(O)$_s$Me or S(O)$_s$CF$_3$, for example where s is 2, OMe, NO$_2$, CO$_2$H, CO$_2$Me, CN or, when n is 2, X is OH, SH or NH$_2$, $R^2$ is a group (A) as defined above, x is zero, $R^6$ is trifluoromethyl, and $R^3$, $R^4$ and $R^5$ are each hydrogen atoms.

A further preferred class of compounds of formula (I) are those wherein $R^1$ is O—$(CH_2)_n OC_{1-4}$alkyl, such as O—$(CH_2)_n$OMe, for example OCH$_2$OMe or O—CH$_2$CH$_2$OMe, $R^2$ is a group (A) as defined above, x is zero, $R^3$, $R^4$ and $R^5$ are hydrogen atoms, and $R^6$ is trifluoromethyl.

Specific compounds according to the invention include:
(2-Cyclopentoxy-5-tetrazol-1-yl)benzyl)-([2S,3S]-2-phenylpiperidin-3-yl)amine;
(2-Cyclopropylmethoxy-5-tetrazol-1-yl)benzyl)-([2S,3S]-2-phenylpiperidin-3 -yl)amine;
(2-Cyclopentoxy-5-(5-trifluoromethyltetrazol-1-yl)benzyl)-([2S,3S]-2-phenyl piperidine-3-yl)amine;
(2-Cyclopropylmethoxy-5-(5-trifluoromethyltetrazol-1-yl)benzyl)-([2S,3S]-2 -phenylpiperidin-3-yl)amine;
(2-Fluoromethoxy-5-(5-trifluoromethyltetrazol-1-yl)benzyl)-([2S,3S]-2 -phenylpiperidin-3-yl)amine;
[2-(2-methoxy-1-ethoxy)-5-(5-trifluoromethyl-tetrazol-1-yl)-benzyl]-([2S,3S]-2-phenylpiperidine-3-yl)amine
and pharmaceutically acceptable salts, especially the dihydrochloride salts, and solvates thereof.

Further specific compounds according to the invention include:
(2-Cyclopentoxy-5-(5-methyltetrazol-1-yl)benzyl)-([2S, 3S]-2-phenylpiperidin-3-yl)amine;
(2-Trifluoromethoxy-5-tetrazol-1-ylbenzyl)-([2S,3S]-2-phenylpiperidin-3-yl)amine;
(2-Trifluoromethoxy-5-5-methyltetrazol-1-yl)benzyl)-([2S, 3S]-2-phenylpiperidin-3-yl)amine;

(2-Trifluoromethoxy-5-(5-trifluoromethyltetrazol-1-yl)
benzyl)-([2S,3S]-2-phenylpiperidin-3-yl)amine;
(2-Difluoromethoxy-5-tetrazol-1-ylbenzyl)-([2S,3S]-2-
phenylpiperidin-3-yl)amine;
(2-Difluoromethoxy-5-(5-methyltetrazol-1-yl)benzyl)-([2S,
3S]-2-phenylpiperidin-3-yl)amine;
(2-Difluoromethoxy-5-(5trifluoromethyltetrazol-1-yl)
benzyl)-([2S,3S]-2-phenylpiperidin-3-yl)amine;
(2-(2,2,2-Trifluoroethoxy)-5-tetrazol-1-ylbenzyl)-([2S,3S]-
2-phenylpiperidin-3-yl)amine;
(2-(2,2,2-Trifluoroethoxy)-5-(5-methyltetrazol-1-yl)
benzyl)-([2S,3S]-2-phenylpiperidin-3-yl)amine;
(2-(2,2,2-Trifluoroethoxy)-5-(5-trifluoromethyltetrazol-1-
yl)benzyl)-([2S,3S]-2-phenylpiperidin-3-yl)amine;
(2-Cyclopropylmethoxy-5-(5-methyltetrazol-1-yl)benzyl)-
([2S,3S]-2-phenylpiperidin-3-yl)amine;
and pharmaceutically acceptable salts and solvates thereof.

The compounds of the invention are antagonists of tachykinins, including substance P and other neurokinins both in vitro and in vivo and are thus of use in the treatment of conditions mediated by tachykinins, including substance P and other neurokinins.

The compounds of the invention possess $NK_1$- receptor binding affinity as determined in vitro by their ability to displace [3H]- substance P (SP) from recombinant human $NK_1$ receptors expressed in Chinese Hamster Ovary (CHO) cell membranes. CHO membranes (3–5 µg protein per tube) were prepared and incubated with [3H]-SP (0.6–0.8 nM) at 20° C. for 40 min. Non-specific binding was defined as that remaining in the presence of 1 µM (+) CP99,994.

The compounds of the invention have been shown to have anti-emetic activity as indicated by for example their ability to inhibit radiation-induced emesis in the ferret. In this model of emesis the onset of retching and vomiting occurs approximately 20 minutes after whole body irradiation (2 Grey≡200 Rads). The test compound is administered (e.g. i.p, p.o., i.v., s.c) immediately after irradiation and its effect on emesis determined by comparison with appropriate controls. Anti-emetic activity may also be demonstrated using other emetogens such as cisplatin and ipecacuanha. Alternatively, the test compounds may be administered before irradiation or before treatment with an emetogen, for example 1.5, 3 or 6 hours before irradiation.

The compounds of the invention are potent and specific $NK_1$ antagonists. Furthermore, they exhibit good oral bioavailability and have an advantageous duration of action.

Compounds of the invention are useful as analgesics in particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica: angina; ankylosing spondyolitis; gout; bums; scar pain; itch; and thalamic pain such as post stroke thalamic pain.

Compounds of the invention are also useful as antiinflammatory agents in particular they are useful in the treatment of inflammation in asthma, influenza, chronic bronchitis and rheumatoid arthritis: in the treatment of inflammatory diseases of the gastrointestinal tract such as Crohn's disease, ulcerative colitis, inflammatory bowel disease, non-steroidal anti-inflammatory drug induced damage and inflammatory and secretory effects of bacterial infection, e.g. due to *Clostridium difficile*; inflammatory diseases of the skin such as herpes and eczema; inflammatory diseases of the bladder such as cystitis and urge (i.e. urinary) incontinence; and eye and dental inflammation, e.g. gingivitis and periodontitis.

Compounds of the invention are also useful in the treatment of allergic disorders in particular allergic disorders of the skin such as urticaria, and allergic disorders of the airways such as rhinitis.

Compounds of the invention may also be useful in the treatment of CNS disorders in particular psychoses such as schizophrenia, mania or dementia; cognitive disorders e.g. Alzheimer's disease; anxiety; AIDS related dementia; diabetic neuropathy; multiple sclerosis; depression; Parkinson's disease; and dependency on drugs or substances of abuse; and also the compounds of the invention may act as myorelaxants and antispasmodics.

Compounds of the invention are also useful in the treatment of emesis, i.e. nausea, retching and vomiting. Emesis includes acute emesis, delayed or late emesis and anticipatory emesis. The compounds of the invention, are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5- fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; carcinoid syndrome; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease. post-operative sickness; dialysis-induced emesis; prostaglandin-induced emesis; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; gastro-oesophageal reflux disease, acid indigestion, overindulgence of food or drink, acid stomach, sour stomach, waterbrash/regurgitation, heartburn, such as episodic heartburn, nocturnal heartburn, and meal-induced heartburn and dyspepsia; organ failure, such as in terminal illness; AIDS and AIDS-related conditions, and treatments thereof; and cyclic vomiting syndrome.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), transdermal, depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents.

Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

For transdermal administration the compounds according to the invention may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

The compositions may contain from 0.1% upwards, e.g. 0.1–99% of the active material, depending on the method of administration. A proposed dose of the compounds of the invention is 0.05 mg/kg to about 400 mg/kg bodyweight per day e.g. 0.05 mg/kg to 5 mg/kg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

The compounds of formula (I) may, if desired, be administered with one or more therapeutic agents and formulated for administration by any convenient route in a conventional manner. Appropriate doses will be readily appreciated by those skilled in the art. For example, the compounds of formula (I) may be administered in combination with a systematic anti-inflammatory corticosteroid such as methyl prednisolone or dexamethasone, or a $5HT_3$ antagonist such as ondansetron, granisetron or metoclopramide. The compounds of formula (I) may also be administered in combination with sympathomimetics, such as ephedrine, pseudoephedrine and oxymetazoline, or the compounds may be administered with conventional analgesics, such as non-steroidal antiinflammatory drugs (NSAIDs), opioids or local anaesthetics. Compounds which are specific antagonists at $NK_1$ receptors, such as the compounds of formula (I), may be administered in combination with compounds which are specific antagonists at $NK_2$ receptors.

Compounds of formula (I), and salts and solvates thereof, may be prepared by the general methods outlined hereinafter. In the following description, the groups $R^1$, $R^2$, $R^3$, $R^4$ and $R^5$ and x are as previously defined for compounds of formula (I) unless otherwise stated.

According to a first general process (A), a compound of formula (I) may be prepared by reacting a compound of formula (II):

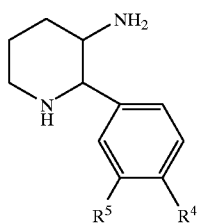

(II)

with a compound of formula (III)

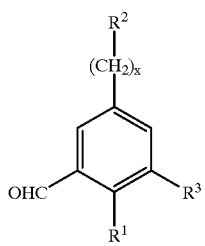

(III)

to form the intermediate imine, which may be isolated if required, followed by reduction of the imine using a suitable reducing agent such as a metal hydride, for example a borane hydride, alane hydride or a metal hydride complex like lithium aluminum hydride or sodium borohydride, or an organo-metallic complex such as borane- methyl sulphide, 9-borabicyclononane (9-BBN), triethylsilane, sodium triacetoxyborohydride, sodium cyanoborohydride and the like. Alternatively, catalytic hydrogenation may be used, for example using a platinum catalyst in a suitable solvent e.g. ethanol.

The condensation reaction conveniently takes place in a suitable solvent such as an alcohol (e.g. methanol), an aromatic hydrocarbon (e.g. benzene, toluene or xylene) or a chlorinated hydrocarbon (e.g. dichloromethane or dichloroethane) at a temperature ranging from ambient to the reflux temperature of the reaction mixture. The reaction preferably takes place in the presence of a catalytic amount of a suitable acidic condensing agent such as p-toluenesulphonic acid or acetic acid and/or a dehydrating agent such as molecular sieves, or the reaction may take place under Dean-Stark conditions.

The reduction step conveniently takes place in a suitable solvent such as acetonitrile, dimethylformamide, benzene, chlorinated hydrocarbons such as dichloromethane or dichloroethane, ethers such as diethyl ether, tetrahydrofuran, dioxane and 1,2-dimethoxyethane and alcohols such as ethanol at a temperature ranging from 0° C. to the reflux temperature of the reaction mixture.

Process (A) may also take place in one step without isolation of the intermediate imine if the condensation reaction takes place in the presence of sodium cyanoborohydride or sodium triacetoxyborohydride. Further reduction is therefore unnecessary in this case.

When carrying out process (A) where $R^2$ is a group (C) as defined hereinbefore, $R^6$ is preferably a $C_{1-4}$alkyl group.

Compounds of formula (II) may be prepared by reducing compounds of formula (IV)

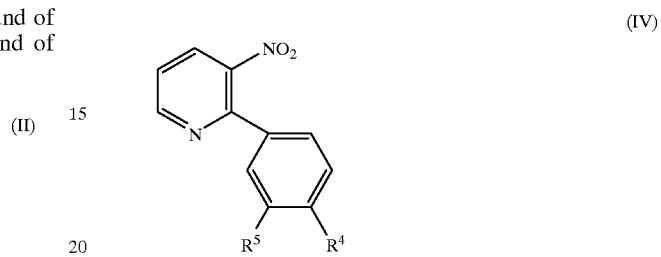

(IV)

under suitable reducing conditions, such as catalytic hydrogenation, for example using a platinum catalyst, e.g. platinum (IV) oxide, in a suitable solvent like ethanol, preferably in the presence of concentrated hydrochloric acid.

Compounds of formula (IV) may be prepared by reacting 2-chloro-3-nitropyridine with a compound of formula (V)

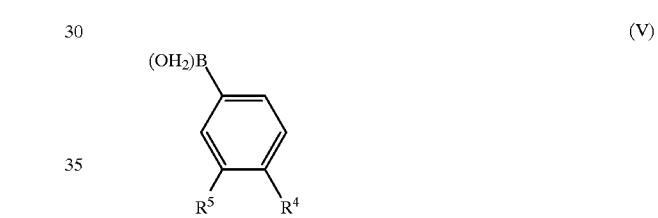

(V)

in the presence of a palladium (O) catalyst such as tetrakis (triphenyl phosphine) palladium (O). The reaction suitably takes place in the presence of a solvent such as an ether, e.g. dimethoxyethane, at an elevated temperature and preferably in the presence of a base such as sodium carbonate.

Compounds of formula (V) may be prepared by reacting the corresponding bromo-compounds under Grignard conditions followed by reaction with tri-isopropylborate.

Alternatively, compounds of formula (II) may be prepared by reducing compounds of formula (VI)

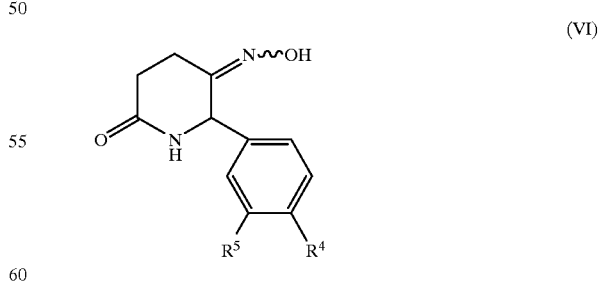

(VI)

under suitable reducing conditions, for example using a metal hydride complex such as sodium borohydride in the presence of zirconium (IV) chloride in a suitable solvent such as tetrahydrofuran.

Compounds of formula (VI) may be prepared by reacting compounds of formula (VII)

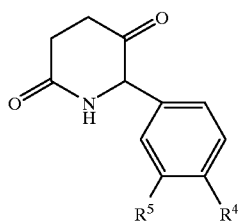

(VII)

with hydroxylamine hydrochloride in the presence of pyridine.

Compounds of formula (VII) may be prepared by reacting compounds of formula (VIII)

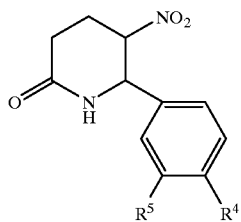

(VIII)

with ozone in the presence of potassium t-butoxide in a suitable solvent such as a mixture of dichloromethane and methanol.

Compounds of formula (VII) may be prepared by reacting compounds of formula (IX)

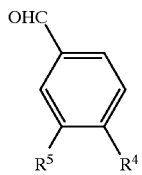

(IX)

with methyl-4-nitrobutyrate and ammonium acetate, in a suitable solvent such as an alcohol, e.g. ethanol at elevated temperature.

Compounds of formula (III), except where $R^1$ represents cyclopropyloxy, cyclobutyloxy or trifluoromethyloxy, may be prepared by reacting compounds of formula (X)

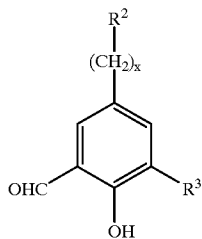

(X)

with an appropriate alkylating agent, such as $(CH_2)_pC_{3-7}$cycloalkyl bromide or iodide or $C_{1-7}$fluoroalkyl chloride, bromide or iodide, in the presence of a base such as potassium carbonate.

Compounds of formula (III) where $R^1$ represents 2,2,2-trifluoroethyloxy may be prepared by reacting compounds of formula (X) with $CF_3CH_2OSO_2R^a$, where $R^a$ represents methyl, paratoluyl or trifluoromethyl, in the presence of hexamethylphosphoramide and potassium carbonate at elevated temperature.

Compounds of formula (III) where $R^1$ represents trifluoromethyloxy may be prepared by reacting compounds of formula (X), or a protected aldehyde thereof, with carbondisulphide and methyl iodide to give the xanthate derivative. The xanthate derivative is then treated with hydrogenfluoride-pyridine complex and deprotected if necessary, to give the required compound of formula (III).

Compounds of formula (III) where $R^1$ represents cyclopropyloxy may be prepared by reacting compounds of formula (X), or a protected aldehyde thereof, with ethylvinyl ether in the presence of mercury acetate. The resulting vinyl derivative is treated with diiodomethane and diethylzinc and deprotected if necessary, to give the required compound of formula (III).

Compounds of formula (III) where $R^1$ represents cyclobutyloxy may be prepared by reacting compounds of formula (XI)

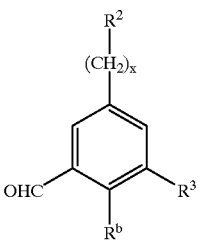

(XI)

where $R^b$ is a suitable leaving group, such as $CF_3SO_3$, or a protected aldehyde thereof, with cyclobutanol in the presence of a base, such as sodium hydride, and a solvent such as dimethylformamide, followed by deprotection where necessary.

Compounds of formula (XI) may be prepared by conventional methods. For example, compounds of formula (XI) where $R^b$ is $CF_3SO_3$ may be prepared by reacting compounds of formula (X) with trifluoromethanesulphonic anhydride in the presence of a base, such as triethylamine.

Compounds of formula (X) may be prepared by reacting compounds of formula (XII)

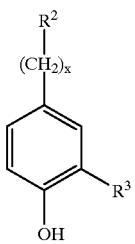

(XII)

with hexamethylenetetramine in the presence of trifluoroacetic acid at elevated temperature.

Compounds of formula (XII) where $R^2$ is a group (A) as define, hereinbefore and x is zero may be prepared by reacting the appropriate p-hydroxyaniline, or a protected derivative thereof, with compounds of formula (XIII)

$$R^6-C(OR^9)_3 \tag{XIII}$$

(where $R^9$ is methyl or ethyl), for example triethylorthoacetate, in acetic acid followed by reaction with sodium azide at elevated temperature and deprotection if necessary.

Compounds of formula (XII) where $R^2$ is a group (A) as defined hereinbefore and x is zero may also be prepared by reacting a compound of formula (XIV)

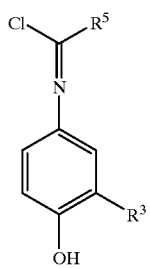

(XIV)

or a protected derivative thereof, with sodium azide in acetic acid at elevated temperature, followed by deprotection if necessary.

Compounds of formula (XIV) may be prepared by reacting a compound of formula (XV)

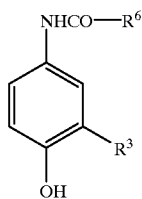

(XV)

or a protected derivative thereof, with resin-supported triphenylphosphine in carbon tetrachloride at elevated temperature.

Compounds of formula (XV) may be prepared by reacting the appropriate p-hydroxyaniline, or a protected derivative thereof, with the appropriate acid chloride or anhydride, i.e. $R^6$—COCl or $R^6$—CO.O.CO—$R^6$, for example trifluoroacetic anhydride, cyclopropane carbonyl chloride, or difluoroacetic anhydride (or the activated acid may be prepared in situ from difluoroacetic acid and e.g. dicyclohexylcarbodiimide).

Compounds of formula (XII) where $R^2$ is a group (A) as defined hereinbefore and x is zero, or protected derivatives thereof, may alternatively be prepared by reacting compounds of formula (XV), or protected derivatives thereof, with an acid anhydride such as trifluoroacetic anhydride or trifluoromethane sulfonic anhydride and sodium azide in acetonitrile.

Compounds of formula (III) where $R^2$ is a group (A) as defined hereinbefore, x is zero and $R^6$ is —$NH_2$ may alternatively be prepared by reacting compounds of formula (XVI)

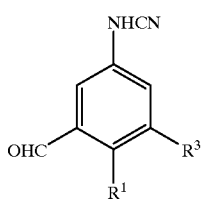

(XVI)

or a protected derivative thereof, with ammonium chloride and sodium azide at elevated temperature, suitably in a solvent such as dimethylformamide, followed by deprotection where required.

Compounds of formula (XVI) may be prepared by reacting compounds of formula (III) where $R^2$ is a group (A) as defined hereinbefore, x is zero and $R^6$ is hydrogen, or a protected derivative thereof, with n-butyl lithium in a suitable solvent such as tetrahydrofuran.

Compounds of formula (III), or protected derivatives thereof, where $R^6$ represents one group may be converted into other compounds of formula (III), or protected derivatives thereof, where $R^6$ represents a different group using conventional procedures, such as alkylation, acylation or oxidation.

Compounds of formula (III) may alternatively be prepared by oxidising compounds of formula (XVII)

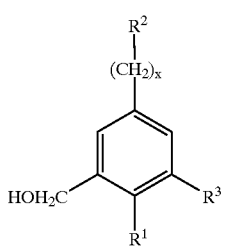

(XVII)

with a suitable oxidising agent such as manganese dioxide in a suitable solvent such as an ether, e.g. tetrahydrofuran, at elevated temperature.

Compounds of formula (XVII), except where $R^6$ is a cyano group, may be prepared by reducing compounds of formula (XVIII)

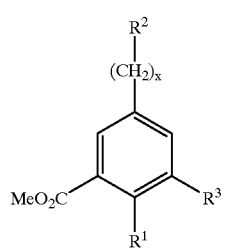

(XVIII)

with a suitable reducing agent such as a metal hydride complex such as lithium borohydride in a suitable solvent such as an ether, e.g. tetrahydrofuran, or an alcohol, e.g. ethanol, or a mixture thereof.

Compounds of formula (XVIII) where $R^2$ is a group (A) as defined hereinbefore and x is zero may be prepared from the corresponding 2-alkoxy-5-amino benzoic acid methyl ester by reacting with compounds of formula (XIII) as defined above, e.g. triethyl orthoformate, and sodium azide in glacial acetic acid and dimethylform-amide at elevated temperature.

Suitable 2-alkoxy-5-amino benzoic acid methyl esters are either known or may be prepared according to methods known for the preparation of known compounds e.g. the method described by Bergman et al in CanJ.Chem, (1973), 51, 162–70.

Compounds of formula (III) where $R^2$ is a group (A) or (B) as defined hereinbefore and x is 1, may be prepared by reacting compounds of formula (XIX)

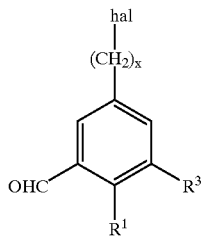

(XIX)

(where hal is a halogen, e.g. bromine or chlorine, atom) with tetrazole in the presence of a base such as triethylamine or potassium carbonate in a suitable solvent such as dichloromethane or dimethylformamide.

Compounds of formula (XIX) where x is 1 may be prepared by reacting compounds of formula (XX)

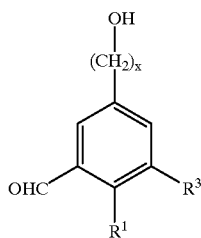

(XX)

or a protected derivative thereof, with a carbon tetrahalide, e.g. carbon tetrabromide, in the presence of triphenylphosphine and a suitable solvent such as ether, followed by deprotection where required.

Compounds of formula (XX) may be prepared by reduction of the corresponding aldehydes after protection of the aldehyde group ortho to $R^1$.

Compounds of formula (XII) where $R^2$ is a group (B) and x is zero may be prepared by reacting the appropriate 1-fluoro-4-nitrobenzene with IH-tetrazole in a suitable solvent at elevated temperature, followed by reduction of the nitro group by catalytic hydrogenation, followed by conversion of the resulting amino function into an alcohol function using nitrous acid.

Compounds of formula (III) where $R^2$ is a group (C) as defined hereinbefore may be prepared by reacting a compound of formula (XXI)

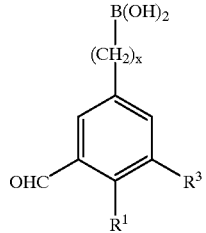

(XXI)

with a compound of formula (XXII)

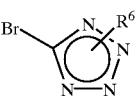

(XXII)

in the presence of a palladium (O) catalyst such as tetrakis (triphenylphosphine) palladium (O) in a suitable solvent such as an ether (e.g. dimethoxyethane) at an elevated temperature.

Compounds of formula (XXI) may be prepared according to similar methods for the preparation of compounds of formula (V) above.

Alternatively, compounds of formula (III) where $R^2$ is a group (C) as defined hereinbefore, x is zero and $R^6$ is hydrogen may be prepared by reacting compounds of formula (XXIII)

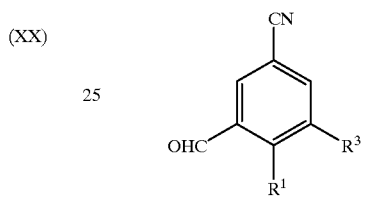

(XXIII)

or a protected derivative thereof, with tributyltinazide at elevated temperature, followed by deprotection where necessary.

Compounds of formula (XXIII) may be prepared from the appropriate p-hydroxybenzonitrile and hexamethylenetetramine as described above for the preparation of compounds of formula (X) from compounds (XII).

According to a further general process (B), compounds of formula (I) where $R^2$ is a group (A) as defined hereinbefore, x is zero and $R^6$ is —$NH_2$ may be prepared by reacting compounds of formula (XXIV)

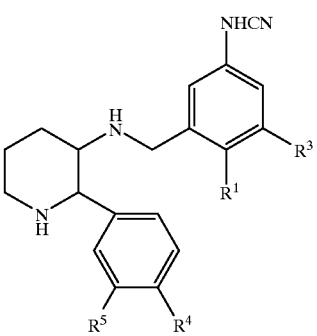

(XXIV)

with ammonium chloride and sodium azide under conditions as described above for the preparation of compounds of formula (III) from compounds of formula (XVI).

Compounds of formula (XXIV) may be prepared by reacting compounds of formula (XVI) with compounds of formula (III) under conditions as described above for process (A).

According to a further general process (C), compounds of formula (I) may be prepared by reduction of compounds of formula (XXV)

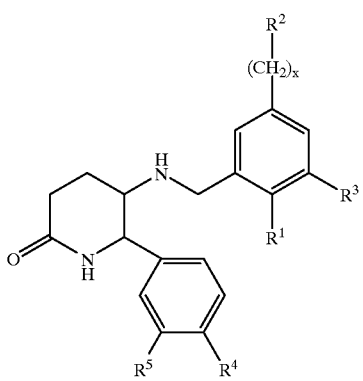

(XXV)

with a suitable reducing agent, such as a metal hydride, for example a borane hydride, in a suitable solvent such as an ether, e.g. tetrahydrofuran, at ambient temperature.

Compounds of formula (XXV) may be prepared by reacting compounds of formula (III) with compounds of formula (XXVI)

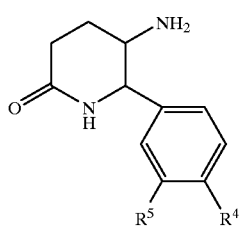

(XXVI)

under conditions as described above for process (A).

Compounds of formula (XXVI) are either known or may be prepared according to methods known for the preparation of known compounds, for example according to the method described in European Patent Application No. EP-A-0436334, incorporated herein by reference.

According to a further general process (D) compounds of formula (I), excluding compounds where $R^1$ represents cyclopropyloxy, cyclobutyloxy and trifluoromethyloxy, may be prepared by reacting a compound of formula (XXVII)

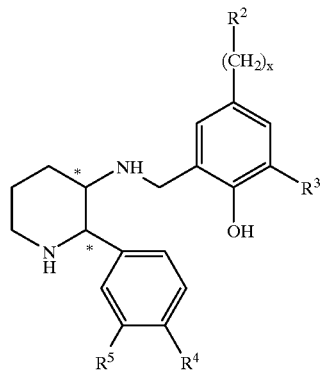

(XXVII)

or an amino-protected derivative thereof, with L—$(CH_2)_p$ $C_{3-7}$cycloalkyl or L—$C_{1-7}$fluoroalkyl where p is as defined hereinbefore and L represents a suitable leaving group such as iodine, bromine, chlorine, $OSO_2R^c{}_1$ where $R^c$ represents methyl, paratoluyl or trifluoromethyl, in the presence of a base, such as potassium carbonate, and a suitable solvent, such as dimethylformamide, at a temperature between 0 and 100° C., e.g. at room temperature, followed by deprotection where necessary.

Compounds of formula (XXVII) may be prepared by reacting compounds of formula (XXVIII)

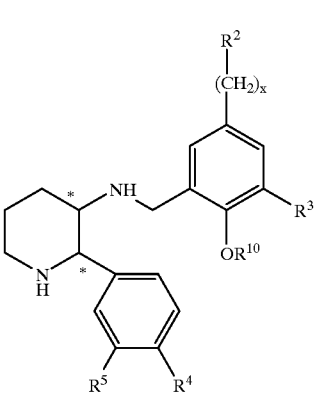

(XXVIII)

where $R^{10}$ is $C_{1-4}$ alkyl, e.g. methyl, with borane-methyl sulphide complex in a suitable solvent, such as dichloromethane, at elevated temperature.

Compounds of formula (XXVIII) may be prepared according to similar methods described herein for the preparation of compounds of formula (I) and those methods described in PCT patent application no. PCT/EP94/03129.

According to a further general process (E) compounds of formula (I) where $R^2$ is a group A as defined above and $R^6$ represents cyano may be prepared by reacting a compound of formula (XXIX)

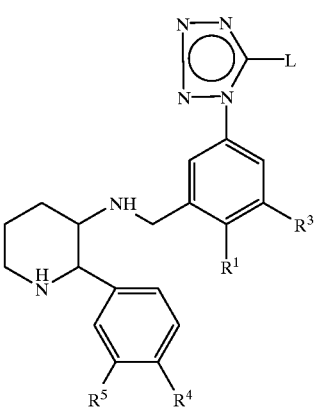

(XXIX)

where L represents a suitable leaving group, such as a methylsulphonyl group, with potassium cyanide. The reaction conveniently takes place at elevated temperature and in the presence of a suitable solvent, such as an alcohol, e.g. ethanol.

Compounds of formula (XXIX) may be prepared by the methods described in processes (A) to (D) described hereinbefore from the appropriately substituted intermediates and also from those methods described in PCT parent application no. PCT/EP94/03129.

Suitable protecting groups for the hydroxyl function include benzyl groups which may be introduced and removed according to conventional procedures. For example deprotection may be effected by catalytic hydrogenation.

Aldehyde functions may be protected as acetals which may be introduced and removed according to conventional procedures. For example, deprotection may be effected by acid hydrolysis.

Amino functions may be protected by, for example, a t-butyl carbamate (BOC) group or a benzyl group which may be introduced and removed according to conventional procedures. For example, deprotection of BOC groups may be effected by acid hydrolysis.

Compounds of formulae (III), (XVI), (XVII), (XVIII), (XXIV), (XXV), (XXVII) and (XXIX) are novel and therefore form a further feature of the invention.

Where it is desired to isolate a compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compound of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, in one example an appropriate optically active acid may be used to form salts with the enantiomeric mixture of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

A particularly suitable route for the preparation of optically active intermediates of formula (II) from the enantiomeric mixture thereof is by fractional crystallisation using (2R, 3R)-bis-(4methyl-benzoyloxy)-succinic acid. Thus, the cis (S,S) form of intermediate (II) may be obtained from an enantiomeric mixture thereof (e.g. the racemic mixture) by fractional crystallisation with (2R, 3R)-bis-4-methyl-benzoyloxy)-succinic acid in a suitable solvent, such as an aqueous alcohol, e.g. aqueous ethanol, isolating the resulting salt and converting it into the corresponding optically active free base by conventional procedures for example using aqueous ammonia.

Alternative methods for preparing and resolving 2-phenyl-3-aminopiperidine are described in PCT patent application no. WO 94/27966, incorporated herein by reference.

Specific enantiomers of a compound of formula (I) may also be obtained by chromatography of the corresponding enantiomeric mixture on a chiral column, for example by chiral preparative h.p.l.c.

Specific diastereoisomers of a compound of general formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which can then be separated by conventional means e.g. by chromatography or by fractional crystallisation. Alternatively, the diastereosiomers may be separable without the need for further derivatization.

Standard resolving methods are described for example in 'Steidochemistry of Carbon Compounds' by E. L. Eliel (McGraw Hill, 1962) and 'Tables of Resolving Agents' by S. H. Wilen.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples which are not intended as a limitation of the invention. All temperatures are in ° C. Flash column chromatography (FCC) was carried out on silica (Merck 3385). The following abbreviations are used: ether-diethyl ether.

Intermediate 1

4-Tetrazol-1-yl-phenol

To a stirred solution of p-amino-phenol (0.1 mol) in glacial acetic acid (140 ml) at 70–75° under nitrogen atmosphere was added triethylorthoformate (0.1 mol). The mixture was stirred at this temperature for 4 h, then, sodium azide (0.32 mol) was added portionwise and the reaction was continued for 18 h, cooled to room temperature and poured into ice water (400 ml) and extracted with diethyl ether (3×400 ml) and ethyl acetate (1×400 ml), dried (MgSO$_4$), filtered and concentrated to give a dark brown residue which was triturated with 200 ml of a mixture of ethanol:diethyl ether (1:1 v/v) and filtered to afford the title compound in 30% yield.

T.I.c. (ether) Rf 0.65

Intermediate 2

2-Hydroxy-5-tetrazol-1-yl-benzaldehyde

A solution of 4-tetrazol-1-yl-phenol (0.01 mol) in trifluoroacetic acid (20 ml) and hexamethylenetetramine (0.04 mol) was heated at 70° for 18 h, cooled to room temperature and quenched with 2N solution of sulfuric acid (50 ml). The mixture was extracted with ethyl acetate (3×100 ml), dried (MgSO$_4$), filtered and concentrated to give a residue which was purified by FCC (dichloromethane/methanol (9:1)) to afford the title compound in 30% yield.

T.l.c. (dichloromethanelmethanol (9:1)) Rf 0.6

Intermediate 3

2-Cyclopentoxy-5-tetrazol-1-ylbenzaldehyde

A mixture of 2-hydroxy-5tetrazol-1-yl-benzaldehyde (500 mg) and potassium carbonate (431 mg) in dimethylformamide (5 ml) at 20° was treated with cyclopentyl bromide (0.33 ml). After 24 h water (20 ml) was added and the mixture extracted with ethyl acetate (2×25 ml). The organics were washed with water (25 ml) and brine (25 ml) and dried (Na$_2$SO$_4$). Evaporation gave a yellow solid which was purified by FCC (ethyl acetate/cyclohexane (2:1)) to give the title compound, as a yellow solid (334 mg).

$v_{max}$(KBr) 1677 cm$^{-1}$

Similarly prepared:

Intermediate 4
2-Cyclopropylmethoxy-5-tetrazol-1-ylbenzaldehyde

From cyclopropyl methyl bromide (0.3 ml) to give the title compound, as a white solid (164 mg).

$v_{max}$(KBr) 1681 cm$^{-1}$

Intermediate 5
N-(4-Benzyloxy-phenyl)-2,2,2-trifluoro-acetamide

A mixture of 4-benzyloxyaniline hydrochloride (0.19 mol) in dichloromethane (750 ml) at 0° under nitrogen was treated dropwise with trifluoroacetic anhydride (27.6 ml) then triethylamine (60 ml) After 24 h the mixture was poured into t-butyl methyl ether (1.5 l) and was washed with 2N hydrochloric acid (1l). The organic phase was dried (MgSO$_4$) and evaporated in vacuo to give the title compound as a white solid (52.3 g).

T.l.c. (cyclohexanelethylacetate (9:1)) Rf 0.36.

Intermediate 6
(4-Benzyloxy-phenyl)-(1-chloro-2,2,2-trifluoro-ethylidene)-amine A mixture of resin-supported triphenylphosphine (3 mmol triphenylphosphine/g resin; 58.6 g) and N-(4-benzyloxy-phenyl)-2,2,2-trifluoro-acetamide (20.8 g) in carbon tetrachloride (800 ml) was heated to reflux under nitrogen for 18 h. The mixture was allowed to cool then filtered, washing the resin with dichloromethane (1 l) and ether (1 l). The organics were concentrated in vacuo to give the title compound as a yellow solid (20.7 g).

T.l.c. (Cyclohexane/ethyl acetate (9:1)) Rf 0.81

Intermediate 7
1-(4-Benzyloxy-phenyl)-5-trifluoromethyl-1 H-tetrazole (4-Benzyloxy-phenyl)-(1-chloro-2,2,2-trifluoro-ethylidene)-amine (66 mmol) was added to a stirred flask of glacial acetic acid (250 ml) at 70° under nitrogen. After 4 min sodium azide (210 mmol) was added and heating was continued for 3 h. After cooling the mixture was filtered, the filtrate poured into water (750 ml) then extracted with dichloromethane (500 ml x3). The combined organic extracts were dried (Na$_2$SO$_4$) and evaporated in vacuo. Purification by FCC using hexane-ethyl acetate (19:1) gave the title compound as a white solid (14.5 g).

T.l.c. (Cyclohexane/ethyl acetate (19:1) Rf 0.22

Intermediate 8
4-(5-Trifluoromethyl-tetrazol-1-yl)-phenol

A solution of 1(4-benzyloxy-phenyl)-5-trifluoromethyl-1H-tetrazole (45.3 mmol) in ethanol (100 ml) and tetrahydrofuran (100 ml) was hydrogenated at room temperature and atmospheric pressure over 10% palladium-carbon catalyst (6 g). After 2 h, the mixture was filtered and the filtrate was evaporated to give the title compound (10.4 g) as a cream solid.

T.I.c. (Dichlormethanelethanol/ammonia(200:8:1)) Rf 0.3.

Intermediate 9
2-Hydroxy-5-(5-trifluoromethyl-tetrazol-1-yl)-benzaldehyde

A solution of 4-(5-trifluoromethyl-tetrazol-1-yl)-phenol (45 mmol) in trifluoroacetic acid (200 ml) and hexamethyl-enetetramine (186.9 mmol) was heated at 100° under nitrogen for 16 h. The reaction mixture was quenched with 2N sulphuric acid (250 ml) and extracted with ether (3x250 ml)). The combined organics were dried (Na$_2$SO$_4$) and evaporated to give a dark yellow oil. Purification by FCC (hexane/ether (2:1)) afforded the title compound (8.8 g) as a pale yellow solid.

T.l.c. (hexane/ether (2:1)) Rf 0.36

Intermediate 10
2-Methoxy-5-(5-trifluoromethyl-etrazol-1-yl)-benzaldehyde

A mixture of 2-hydroxy-5-(5trifluoromethyl-tetrazol-1-yl)-benzaldehyde (1.56 mmol), potassium carbonate (7.8 mmol) and methyl iodide (7.8 mmol), in acetone (25 ml) was stirred for 18 h at 23° under nitrogen. Water (150 ml) was added and the mixture extracted with diethyl ether (3x50 ml). The combined organic extracts were washed with saturated brine, dried (Na$_2$SO$_4$) and evaporated to give the title compound as a yellow solid (0.48 g).

T.l.c. (ether/hexane (2:1)) Rf 0.38.

Intermediate 11
[2-Methoxy-5-(5-trifluoromethyl-tetrazol-1-yl)-benzyl]-([2S,3S]-2-phenyl-piperidine-3-yl)-amine dihydrochloride A mixture of [2S]-phenyl-piperidin -[3S]-ylamine (1.14 mmol), 2-methoxy-5-(5-trifluoromethyl-tetrazol-1-yl)-benzaldehyde (1.2 mmol), sodium triacetoxyborohydride (2.37 mmol) and acetic acid (3 drops) in dichloromethane (25 ml) was stirred at 23° under nitrogen for 64 h. 2N sodium carbonate solution (50 ml) was added and the mixture extracted with dichloromethane (3x25 ml). The combined extracts were washed with saturated brine (50 ml), dried (MgSO$_4$) and evaporated. Purification by FCC with dichloromethane/ethanol/ammonia (400:10:1→100:10:1) gave a colourless viscous oil. This was dissolved in methanol (10 ml) and treated with 2N ethereal hydrogen chloride (~10 ml). Evaporation in vacuo and trituration with i-propyl acetate gave the title compound as a white solid (210 mg).

T.l.c. (Dichloromethanetethanol/ammonia (200:10:1)) Rf 0.39.

Optical Rotation (c 3 mg/ml. water) +50.35°.

Intermediate 12
[2-Hydroxy-5-(5-trifluoromethyl-tetrazol-1-yl)-benzyl]-([2S, 3S]-2-phenylpiperidin-3-yl)amine A suspension of [2-methoxy-5-(5-trifluoromethyl-tetrazol-1-yl)-benzyl]-([2S,3S]-2-phenylpiperidin-3yi)amine dihydrochloride (1.01 g, 2 mmol) in chloroform (20ml) was stirred at room temperature and treated with triethylamine, (0.58 ml, 406 mg, 4 mmol) to give a clear solution. This was then treated slowly with a solution of boron tribromide: dimethylsulfide complex (20 ml of 1M solution in dichloromethane; 20 mmol) and the reaction mixture was refluxed under nitrogen for 3 days. Further reagent (10 ml, 10 mmol) was then added and after a further 3 days the mixture was cooled in an ice-bath, stirred and treated with methanol (40 ml). The mixture was evaporated to dryness. This treatment was repeated twice further. The resulting oil was partitioned between ethyl acetate (100 ml) and saturated aqueous sodium bicarbonate (100 ml). The aqueous phase was extracted with further ethyl acetate (50 ml) after pH adjustment (to pH ca 8). Combined extracts were washed with brine (100 ml) dried (MgSO$_4$) and evaporated to a brown foam, which was chromatographed on silica (Merck 9385) eluting with 2% then 5% methanol in dichloromethane. The required fractions were combined and evaporated to give the title compound as a light brown foam (672 mg), mass spectrum (thermospray +ve) m/e 419 (MH$^+$).

Intermediate 13
3-{tert-Butoxycarbonyl-[2-hydroxy-5-(5-trifluoromethyl-tetrazol-1-yl)-benzyl]-amino}-[2S,3S]-2-phenylpiperidine-1-carboxylic acid tert-butyl ester A solution of [2-hydroxy-5-(5-trifluoromethyl-tetrazol-1-yl)-benzyl]-([2S,3S]-2-phenylpiperidine-3-yl)amine (418 mg, 1 mmol) in dichloromethane (5 ml) was treated with di-t-butyidicarbonate (240 mg, 1.1 mmol) and the solution was stirred for 19 h at room temperature. Further reagent was then added (240 mg) and after a further day the solution was evaporated to dryness. The resulting gum was chromatographed on silica (Merck 9385; 70 g) eluting with 3:1 then 1:1 cyclohexane:ethyl acetate. The required fractions were combined and evaporated to provide the title compound as a light brown foam (487 mg), ν(CHBr$_3$) 1663 and 1690cm$^{-1}$ (carbamate C=O).

Intermediate 14
3-{tert-Butoxycarbonyl-[2-(cyclopropylmethoxy)-5-(5-trifluoromethyl-tetrazol-1-yl)-benzyl]-amino-}[2S,3S]-2-phenylpiperidine-1-carboxylic acid tert-butyl ester A solution of 3-{tert-butoxycarbonyl-[2-hydroxy-5-5trifluoromethyl-tetrazol-1-yl)-benzyl]-amino)}-[2S,3S]-2-phenylpiperidine-1-carboxylic acid tert-butyl ester (402 mg) in dimethylformamide (1 ml) containing a suspension of finely ground potassium carbonate (89 mg) was stirred at room temperature and treated with cyclopropylmethyl bromide (529 mg). After 11 days stirring at room temperature the mixture was partitioned between ethyl acetate (50 ml) and 2M hydrochloric acid (50 ml). The organic phase was washed with brine (2×50 ml), dried (MgSO$_4$) and evaporated to give a brown gum. This was chromatographed on silica (Merck 9385) eluting with 7:1 then 5:1 cyclohexane-:ethyl acetate to give the title compound as a white foam (104 mg), mass spectrum (electrospray +ve) m/e 673. (MH$^+$).

Intermediate 15
[2-(Fluoromethoxy)-5-(5trifluoromethyl-tetrazol-1-yl)]-benzaldehyde A solution of [2-hydroxy-5-(5-trifluoromethyl)-tetrazol-1-yl)]-benzaldehyde (200 mg, 0.77 mmole) in dimethylformamide (1 ml) containing a suspension of potassium carbonate (107 mg, 0.77 mmol) was stirred in an ice-bath and treated with bromofluoromethane (few mls). Further bromofluoromethane (few mls) was added after 1.5 h and the reaction mixture was allowed to reach room temperature. After 17 h it was partitioned between ethyl acetate (50 ml) and 2M-hydrochloric acid (50 ml) and brine (2×50 ml), dried (MgSO$_4$) and evaporated to the title compound as an off-white solid (211 mg), ν (CHBr$_3$) 1698 cm$^{-1}$ (C=O aldehyde).

Similarly prepared:

Intermediate 16
[2-(2-Cyclopentoxy)-5-(5-trifluoromethyl-tetrazol-1-yl)]-benzaldehyde From [2-hydroxy-5-(5-trifluoromethyl-tetrazol-1-yl)]-benzaldehyde (250 mg, 0.97 mmole) and bromocyclopentane (434 mg, 2.91 mmole) to give the title compound as a pale yellow solid (240 mg), ν (KBr powder) 1687 cm$^{-1}$ (C=O aldehyde).

EXAMPLE 1

(2-Cyclopentoxy-5-tetrazol-1-ylbenzyl)-([2S, 3S]-2-phenylpiperidin-3-yl) amine dihydrochloride To a solution of [2S]-phenylpiperidin-[3S]-ylamine (1.0 mmol) and 2-cyclopentoxy-5-tetrazol-1-ylbenzaldehyde (0.91 mmol) in dichloromethane (4 ml) and acetic acid (1.5 mmol), triacetoxyborohydride (1.30 mmol) was added. After 18 h the solvent was reduced and the residue partitioned between ethyl acetate (25 ml) and 2M sodium carbonate solution (25 ml). The aqueous was re-extracted with ethyl acetate (2×25 ml) and the combined organics dried (Na$_2$SO$_4$) and reduced to an oil. This was dissolved in hot ethanol (8 ml) and conc.HCl added (177 μl). After 4 h the crystals' were harvested and dried in vacuo at 50° overnight to give the title compound (309 mg).

δ(D$_2$O) 1.50–1.80 (6H, m), 1.80–2.00 (2H, m), 2.10–2.20 (2H, m), 2.30 (1H, m) 2.55 (1H, m), 3.35 (1H, m), 3.75 (1H, m), 4.00 (1H, m), 4.15 (1H, d J=18H$_z$), 4.40 (1H, d J=18H$_z$), 4.95 (1H, d J=5H$_z$), 7.15 (3H, m), 7.40 (3H, m), 7.64 (1H, d J=4H$_z$), 7.80 (1H, dd J=11,4 H$_z$), 9.58 (1 H, s).

Assay: Found: C.58.12%; H. 6.34%; N, 17.28%; Cl, 14.1%. C$_{24}$H$_{30}$N$_6$O. 2HCl requires C. 58.65%; H, 6.56%; N, 17.10%; Cl, 14.4%.

Similarly prepared:

EXAMPLE 2

(2-Cyclopropylmethoxy-5-tetrazol-1-ylbenzyl)-([2S, 3S]-2-phenylpiperidin-3-yl) amine dihydrochloride From 2-cyclopropylmethoxy-5tetrazol-1-ylbenzaldehyde (0.59 mmol) and [2S]-phenylpiperidin-[3S]-ylamine (0.65 mmol) to give the title compound (134 mg).

δ(D$_2$O ) 0.30 (2H, m), 0.65 (2H, m), 1.20 (1H, m), 2.00–2.60 (4H, m), 3.35(1 H, m), 3.65–3.90 (3H, m), 4.02 (1H, m), 4.21 (1H, d J=18H$_z$), 4.45 (1H, d J =18H$_z$) 4.98 (1H, d J=5H$_z$), 7.15 (1H, d J=12H$_z$), 7.25 (2H, m), 7.45 (3H, m), 7.62 (1H, m), 7.82 (1 H, dd J=11, 4H$_z$), 9.57 (1 H, s).

Assay: Found: C, 57.70%; H, 6.32%; N, 17.43%, Cl, 14.7%. C$_{23}$H$_{28}$N$_6$O.2HCl requires
C, 57.86%; H, 6.33%; N,17.60%; Cl, 14.9%.

EXAMPLE 3

[2(CycloPropylmethoxy)-5-(5-trifluoromethyl-tetrazol-1-yl)-benzyl]-([2S, 3S]-2-phenylpiperidin-3-yl)amine dihydrochloride A solution of 3-{tert-butoxycarbonyl-[2-(cyclopropylmethoxy)-5-(5-trifluoromethyl-tetrazol-1-yl)-benzyl]-amino}[2S,3S]-2-phenylpiperidine-1-carboxylic acid tertbutyl ester (101 mg, 0.15 mmole) in 4M-hydrogen chloride in dioxan (5 ml) was kept at 44° for 3.25 h and then evaporated. The residue was triturated with ethanol to give the title compound as a white solid (66 mg), mass spectrum (thermospray +ve) m/e 473 (MH$^+$). R$_F$ 0.5 (100: 8:1 dichloromethane: ethanol: ammonia).

EXAMPLE 4

[2-(Fluoromethoxy)-5-(5-trifluoromethyl-tetrazol-1-yl)-benzyl]-([2S,3S]-2-phenylriperidin-3-yl)amine dihydrochloride A suspension of ([2S, 3S]-2-phenylpiperidin-3-yl)amine dihydrochloride (90 mg, 0.36 mmole) in dichloromethane (2 ml) containing [2-(fluoromethoxy)-5-(5-trifluoromethyl-tetrazol-1-yl)]-benzaldehyde (104 mg, 0.36 mmole) was stirred at room temperature and treated with triethylamine (73 mg, 0.72 mmole) to give a solution. Glacial acetic acid (22 mg, 0.36 mmole) and sodium triacetoxyborohydride (114 mg, 0.54 mmole) were then added. After 2.75 h the reaction mixture was evaporated to dryness. The residue was partitioned between ethyl acetate (50 ml) and saturated aqueous sodium bicarbonate (50 ml). The aqueous phase was further extracted with ethyl acetate (25 ml). Combined extracts were washed with brine (2×50 ml), dried (MgSO$_4$)

and evaporated to a yellow gum. This was dissolved in hot ethanol (95% ca 3 ml) and the solution was treated with concentrated hydrochloric acid (0.71 mmole) to give white crystals of the title compound (107 mg). Found C, 48.41; H, 4.91; N, 15.68; F,14.52; $C_{21}H_{22}F_4N_6O.2HCl$ (523.4) requires C, 48.19; H, 4.62; N, 16.02%; F,14.26% Mass spectrum (thermospray +ve) m/e 451 (MH$^+$).

Similarly prepared:

EXAMPLE 5

[2-(2-Cyclopentoxy)-5-(5-trifluoromethyl-tetrazol-1-yl)-benzyl]-([2S,3S]-2-phenylpiperidin-3-yl)amine dihydrochloride From [2-(cyclopentoxy)-5-(5-trifluoromethyl-tetrazol-1-yl)]-benzaldehyde (100 mg, 0.32 mmole) and ([2S,3S]-2-phenylpiperidin-3-yl)amine (54 mg, 0.32 mmole) to give the title compound as a cream solid (114 mg), mass spectrum (thermospray +ve) m/e 487 (MH$^+$). R$_F$ 0.41 (100:8:1 dichloromethane: ethanol: ammonia).

EXAMPLE 6 a) 3-{tert-Butoxycarbonyl-[2-(2-methoxy-1-ethoxy)-5-(5-trifluoromethyl-tetrazol-1-yl-benzyl]-amino} [2S,3S]-2-phenylpiperidine-1-carboxylic acid tert-butyl ester A solution of 3-{tert-butoxycarbonyl-[2-hydroxy-5-(5-trifluoromethyl-tetrazol-1-yl)-benzyl]-amino}-[2S,3S]-2-phenylpiperidine-1-carboxylic acid tert-butyl ester (177 mg) in dimethylformamide (0.5 ml) containing a suspension of finely ground potassium carbonate (39 mg) was stirred and treated with 2-chloroethylmethyl ether (280 mg) and potassium iodide (few crystals). The mixture was stirred at 44° for 9 days then at 60° for 2 days. The mixture was partitioned between ethyl acetate (25 ml) and 2M hydrochloric acid (25 ml). The aqueous phase was extracted with ethyl acetate (25 ml) and the combined organic phases were washed with water (25 ml) and brine (2×25 ml), dried (MgSO$_4$) and evaporated to give a brown gum. This was chromatographed on silica (Merck 9385) eluting with 3:1 cyclohexane:ethyl acetate to give the title compound as a white foam (57 mg), mass spectrum (thermospray +ve) m/e 677 MH$^+$). The title compound was deprotected according to conventional procedures to give:

b) [2-(2-methoxy-1-ethoxy)-5-(5-trifluoromethyl-tetrazol-1-yl)-benzyl]-([2S,3S]-2-phenylpiperidine-3-yl)amine A solution of 3-{tert-Butoxycarbonyl-[2-(2-methoxy-1-ethoxy)-5-trifluoromethyl-tetrazol-1-yl)-benzyl]-amino}-[2S,3S]-2-phenylpiperidine-1carboxylic acid tert-butyl ester (54 mg, 0.08 mmol) in 4M hydrogen chloride in dioxan (5 ml) was kept at 44° for 20 h and then evaporated to a white foam (48 mg). Trituration of this material with ether followed by drying at 40° under vacuum gave the title compound (36 mg)

δ(D$_2$O) 2.02 (2H, m), 2.18–2.38 and 2.38–2.58 (2H, 2m), 3.23–3.40 (1H, m), 3.43 (3H, s), 3.65–3.85 (3H, m), 3.91–4.25 (4H, m), 4.43 (1H, d, J=12 Hz), 4.9 (1H, d, J=3Hz), 7.14 (1H, d, J=8Hz), 7.25 (2H, d, J=7Hz), 7.39–7.58 (4H, m), 7.69 (1H, dd, J=8, 2 Hz).

Assay: Found: C, 49.15%; H, 5.25%; N, 14.40%. $C_{23}H_{27}F_3N_6O.C.7H_2O$ requires C, 49.15%; H. 5.45%; N, 14.95%.

PHARMACY EXAMPLES

EXAMPLE A

STERILE FORMULATION

|  | mg/ml |
|---|---|
| Compound of the invention | 0.3 mg |
| Sodium Chloride USP | 6.0 mg |
| Sodium Acetate USP | 2.6 mg |
| Acetic Acid | 1.1 mg |
| Water for Injection USP | qs to 1 ml |

The components are dissolved in a portion of the water for injection and the solution made up to final volume to provide 0.25 mg/ml of the compound of the invention.

The solution may be packaged for injection, for example by filling and sealing in ampoules, vials or syringes. The ampoules, vials or syringes may be aseptically filled and/or terminally sterilised by, for example, autoclaving at 121° C.

Tablets for Oral Administration

Tablets may be prepared by the normal methods such as direct compression or wet granulation.

The tablets may be film coated with suitable film forming materials, such as Opadry White, type YS-1-7027, using standard techniques. Alternatively the tablets may be sugar coated.

EXAMPLE B

| Direct Compression Tablet | mg/Tablet |
|---|---|
| Compound of the invention | 0.6 mg |
| Magnesium Stearate | 0.75 mg |
| Avicel PH102 | qs 150.00 mg |

The compound of the invention is passed through a 30 mesh sieve and blended with Avicel PH102 and magnesium stearate. The resultant mix is compressed into tablets using a suitable tablet machine fitted with ⁹⁄₃₂" diameter punches.

EXAMPLE C

Wet Granulation

A formulation as described in Example B may be used. The compound of the invention (dihydrochloride) is dissolved in a suitable volume of granulating solution (purified water or 10% PVP K29/32 in water). After drying, the granules are screened, for example through 20 mesh screen, and blended with magnesium stearate. The granules are then compressed into tablets as described in Example B.

EXAMPLE D

Suppository

| Compound of the invention | 10.0 mg |
|---|---|
| Witepsol W32, hard fat | qs 2000.0 mg |

Blend micronized drug in a portion of the melted Witepsol W32 at approximately 36° C. for approximately 15 minutes in a high speed mixer. Incorporate the homogenized slurry into the remaining portion of the melted Witepsol W32 and blend at approximately 36° C. until satisfactory dispersion is achieved. Fill moulds with 2000 mg formulation.

EXAMPLE E

Capsule

|  | mg/capsule |
| --- | --- |
| Compound of the invention | 12.0 mg |
| Polyethylene glycol | 92.89 mg |
| Propylene glycol | qs 200 mg |

Blend together polyethylene glycol and propylene glycol using heat as necessary. Stir until homogeneous. Add micronised compound of the invention to blend. Mix until homogenous. Fill into an appropriate gelatin mass to give soft gelatin capsules containing 200 mg of the formulation.

EXAMPLE F

Oral Syrup

|  | mg/ml |
| --- | --- |
| Compound of the invention | 6.0 mg |
| Sucrose | 200 mg |
| Methylparaben | 1.2 mg |
| Propylparaben | 0.15 mg |
| Flavouring | 1.5 mg |
| Citric Acid | 0.1 mg |
| Purified Water | qs 1 ml |

Dissolve the parabens in a small portion of the water that has been heated to approximately 90° C. Add the paraben solution to a large portion of the remaining water with mixing. Add and dissolve the other components. Bring the formulation to final volume and mix until homogenous. Fill the formulation into a container, such as a unit dose cup or a bottle for multiple-dose use.

We claim:

1. A compound of formula (I)

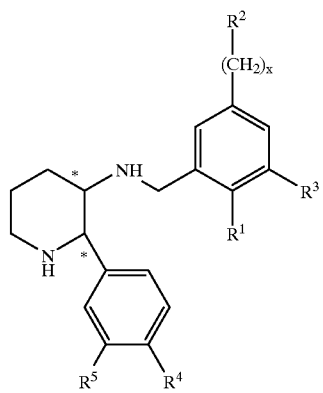

(I)

wherein $R^1$ is —O—$(CH_2)_p$ $C_{3-7}$cycloalkyl, —O—$C_{1-7}$ fluoroalkyl, or —O—$(CH_2)_n$X;

$R^2$ is

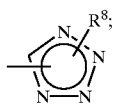

$R^3$ is a hydrogen or halogen atom;

$R^4$ and $R^5$ may each independently represent a hydrogen or halogen atom, or a $C_{1-4}$alkyl, $C_{1-4}$alkoxy or trifluoromethyl group;

X is a C(O)—$NR^7R^8$, C(O)$R^9$, $NR^7R^8$, $SO_2NR^7R^8$, $NHSO_2R^9$, S(O)$_s$ $R^9$, O$C_{1-4}$alkyl, $NO_2$, $CO_2$ H, $CO_2C_{1-4}$alkyl, CN or, when n is 2, X may also represent OH, SH or $NH_2$;

$R^6$ is a hydrogen atom, a $C_{1-4}$alkyl, $(CH_2)_m$cyclopropyl, —S(O)$_s$C$_{1-4}$alkyl, phenyl, $NR^{10}$ $R^{11}$, $CH_2C(O)CF_3$, trifluoromethyl, difluoromethyl or a cyano group;

$R^7$ and $R^8$ may each independently represent hydrogen atoms or a $C_{1-4}$alkyl group;

$R^9$ represents a $C_{1-4}$alkyl or trifluoromethyl group;

$R^{10}$ and $R^{11}$ may each independently represent a hydrogen atom, or a $C_{1-4}$alkyl or acyl group;

x represents zero or 1;

n is 1 or 2;

s represents zero, 1 or 2;

m represents zero or 1;

p represents zero or 1;

or a pharmaceutically acceptable salt or solvate thereof, with the proviso that when $R^1$ is —O—$(CH_2)_n$CHF$_2$ or —O—$(CH_2)_n$CN, $R^2$ is

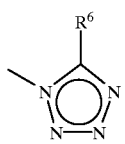

and x is zero.

2. A compound according to claim 1 wherein $R^2$ is

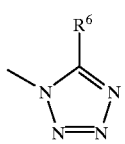

x is zero and $R^3$, $R^4$ and $R^5$ are each hydrogen atoms.

3. A compound according to claim 1 wherein $R^1$ is a cyclopropylmethoxy, cyclopentyloxy, difluoromethyloxy, trifluoromethyloxy, 2,2,2-trifluoroethyloxy, fluoromethyloxy, $OCH_2OMe$ or $O—CH_2CH_2OMe$ group.

4. A compound according to claim 1 wherein $R^6$ is a hydrogen atom or a $C_{1-4}$alkyl or a trifluoromethyl group.

5. A compound which is (2-Cyclopentoxy-5-tetrazol-1-ylbenzyl)-(-2-phenylpiperidin-3-yl)amine;

(2-Cyclopropylmethoxy-5-tetrazol-1-ylbenzyl)-(-2-phenylpiperidin-3-yl)amine;

(2-Cyclopentoxy-5-(5-trifluoromethyltetrazol-1-yl)benzyl)-(-2-phenylpiperidin-3-yl)amine, (2-Cyclopropylmethoxy-5-(5-trifluoromethyltetrazol-1-yl)benzyl)-(-2-phenylpiperidin-3-yl)amine;

(2-Fluoromethoxy-5-(5-trifluoromethyltetrazol-1-yl)benzyl)-(-2-phenylpiperidin-3-yl)amine;

[2-(2-methoxy-1-ethoxy)-5-(5-trifluoromethyl-tetrazol-1-yl)-benzyl]-(-2-phenylpiperidine-3-yl)amine or a pharmaceutically acceptable salt or solvate thereof.

6. A pharmaceutical composition comprising a compound according to claim 1 or a pharmaceutically acceptable salt or solvate thereof, together with a pharmaceutically acceptable carrier.

7. A method for the treatment of a condition mediated by tachykinins, including substance P and other neurokinins, in a mammal wherein the conditions are susceptible to treatment by antagonism of the binding of tachykinin to NK1 receptor comprising administration of an effective amount of a compound according to claim 1, or a pharmaceutically acceptable derivative thereof.

8. A process for preparing a compound of formula (I) as defined in claim 1, or a pharmaceutically acceptable salt or solvate thereof which comprises:

(A) reacting a compound of formula (II)

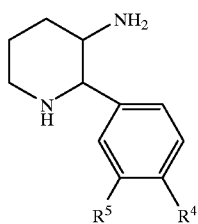

(II)

with a compound of formula (III)

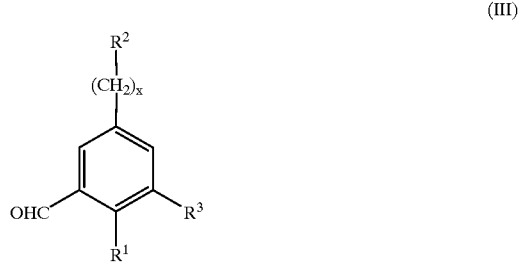

(III)

followed by reduction: or (B) a process for preparing a compound of formula (I) where $R^2$ is a group (A) as defined hereinbefore, x is zero and $R^6$ is —$NH_2$ which comprises reacting a compound of formula (XXIV)

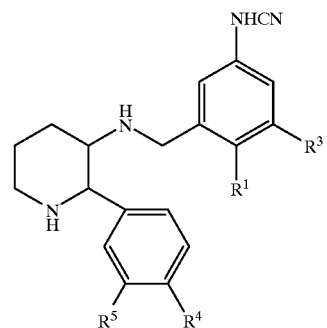

(XXIV)

with ammonium chloride and sodium azide: or (C) reducing a compound of formula (XXV)

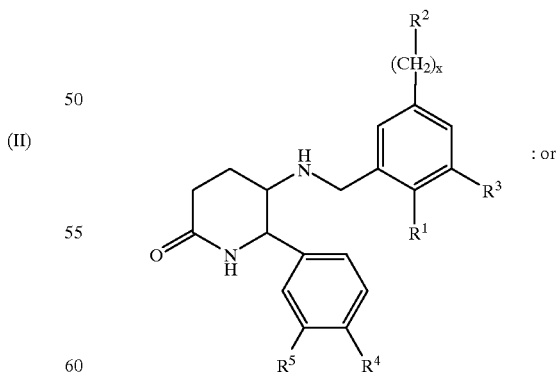

(XXV)

: or (D) a process for preparing compounds of formula (I), excluding compounds where $R^1$ represents cyclopropyloxy, cyclobutyloxy and trifluoromethyloxy which comprises reacting a compound of formula (XXVII)

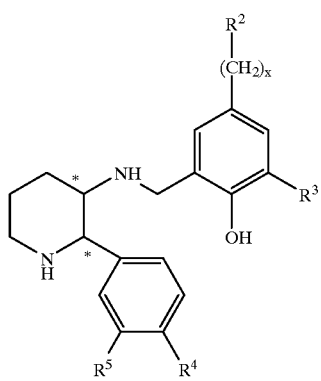

(XXVII)

or an amino-protected derivative thereof, with L-$(CH_2)_pC_{3-7}$ cycloalkyl or L-$C_{1-7}$fluoroalkyl where p is as defined hereinbefore and L represents a suitable leaving group in the presence of a base followed by deprotection where necessary: or (E) a process for preparing compounds of formula (I) where $R^2$ is a group A as defined above and $R^6$ represents cyano which comprises reacting a compound of formula (XXIX)

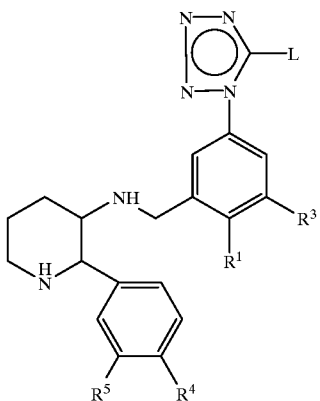

(XXIX)

where L represents a suitable leaving group, with potassium cyanide.

* * * * *